(12) United States Patent
Harkins et al.

(10) Patent No.: US 12,213,952 B1
(45) Date of Patent: *Feb. 4, 2025

(54) BIOLOGIC ENHANCEMENT FORMULATION

(71) Applicant: HEH RESEARCH & DEVELOPMENT SERVICES, INC., Tucson, AZ (US)

(72) Inventors: Stephen J. Harkins, Tucson, AZ (US); Mitchell R. Halter, Tucson, AZ (US)

(73) Assignee: HEH RESEARCH & DEVELOPMENT SERVICES, INC., Tucson, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/412,174

(22) Filed: Jan. 12, 2024

Related U.S. Application Data

(63) Continuation-in-part of application No. 17/244,814, filed on Apr. 29, 2021, now Pat. No. 11,931,323, which is a continuation-in-part of application No. PCT/US2019/062257, filed on Nov. 19, 2019, which is a continuation of application No. 16/195,425, filed on Nov. 19, 2018, now abandoned, which is a continuation-in-part of application No. 15/913,619, filed on Mar. 6, 2018, now abandoned.

(60) Provisional application No. 62/469,376, filed on Mar. 9, 2017.

(51) Int. Cl.
| | |
|---|---|
| A61K 31/00 | (2006.01) |
| A23L 2/56 | (2006.01) |
| A23L 2/60 | (2006.01) |
| A23L 33/155 | (2016.01) |
| A61K 9/00 | (2006.01) |
| A61K 31/122 | (2006.01) |
| A61K 31/401 | (2006.01) |
| A61K 31/706 | (2006.01) |
| A61K 31/7068 | (2006.01) |

(52) U.S. Cl.
CPC .............. *A61K 31/122* (2013.01); *A23L 2/56* (2013.01); *A23L 2/60* (2013.01); *A23L 33/155* (2016.08); *A61K 9/0095* (2013.01); *A61K 31/401* (2013.01); *A61K 31/706* (2013.01); *A61K 31/7068* (2013.01); *A23V 2002/00* (2013.01)

(58) Field of Classification Search
CPC .................................................... A61K 31/00
See application file for complete search history.

(56) References Cited

U.S. PATENT DOCUMENTS

| | | | |
|---|---|---|---|
| 7,169,385 B2 | 1/2007 | Fantuzzi et al. | 424/94.1 |
| 2005/0002992 A1 | 1/2005 | McCleary | A61K 31/198 |
| 2006/0134294 A1 | 6/2006 | McKee | 426/548 |
| 2007/0116838 A1 | 5/2007 | Prakash et al. | 426/548 |
| 2013/0171294 A1 | 7/2013 | Martyn | 426/2 |
| 2014/0037604 A1 | 2/2014 | Greenberg et al. | 424/93.41 |
| 2016/0004298 A1 | 1/2016 | Mazed et al. | G06F 3/011 |
| 2016/0209428 A1* | 7/2016 | Naviaux | G01N 33/6848 |

FOREIGN PATENT DOCUMENTS

| | | | | |
|---|---|---|---|---|
| DE | 202014007740 | 12/2014 | | A23L 33/10 |
| EP | 1677774 | 7/2006 | | |
| JP | 2005261357 | 9/2005 | | A23L 2/00 |
| WO | WO2005006890 | 1/2005 | | A23L 1/29 |

OTHER PUBLICATIONS

U.S. Appl. No. 15/913,619, filed Mar. 6, 2018.
U.S. Appl. No. 16/195,425, filed Nov. 19, 2018.
U.S. Appl. No. 17/244,814, filed Apr. 29, 2021.
U.S. Appl. No. 16/195,425, filed Nov. 19, 2018, Harkins et al.
U.S. Appl. No. 17/244,814, filed Apr. 29, 2021, Harkins et al.
Adibhatla et al., "Citicoline: Neuroprotective Mechanisms in Cerebral Ischemia" *Journal of Neurochemistry* 2002; 80:12-23 (12 pgs).
Adibhatla, R.M et al la., "Mini-Review: Citicoline Mechanisms and Clinial Efficacy in Cerebral Ischemia" *Journal of Neuroscience Research*, 70: 113-139 (2002) (23 pgs).
Alvarez-Sabin J et al. "Long-term Treatment with Citicoline Prevents Cognitive Decline and Predicts a Better Quality of Life After a First Ischemic Stroke" *International Journal of Molecular Sciences* 2016; 17: 1-12 (16 pgs).
Alvarez-Sabin, Jose, MD. et al. "Citicoline in Vascular Cognitivie Impairment and Vascular Dementia After Stroke", *Stroke*, 2011, 42, suppl 1, S40-S43 (10 pgs).
Banerjee et al. "Prolonged Electrical Muscle Stimulation Exercise Improves Strength and Aerobic Capacity in Healthy Sedentary Adults". *J Appl. Physiol.* 2005; 99(6): 2307-2311 (13 pgs).
Belenky et al., "NAD+ metabolism in health and disease" Trends in Biochemical Science vol. 32, No. 1, 2006 (8 pgs).
Betts et al. "Systemic Indicies of Skeletal Muscle Damage and Recovery of Muscle Function After Exercise: Effect of Combined Carbohydrate-Protein Ingestion". *Appl. Physiol. Nutr. Metab.* 2009; 34: 773-784 (12 pgs).

(Continued)

*Primary Examiner* — Rosanne Kosson
(74) *Attorney, Agent, or Firm* — HAYES SOLOWAY P.C.

(57) ABSTRACT

Provided is an "all natural" biologic-enhancing beverage (BioBeverage), which contains, in addition to purified water, electrolytes, vitamins, anti-oxidants, micronutrients, natural fruit infusion, natural sweetener to improve taste, enhance GI Biome viability, provide antimicrobial benefits and reduce oxidative stress, Citicoline, to enhance brain/neurologic function, neurologic maintenance, repair and regeneration, CoQ10, to enhance cardiovascular energy and health, Hydroxyproline, to enhance connective tissue maintenance, repair and regeneration, and a niacinamide adenine dinucleotide (NAD+) precursor to promote overall health, including neurologic, cardiovascular and connective tissues maintenance and repair, and if present, reduce risks and symptoms of multiple neurodegenerative disorders by maintenance of healthy mitochondrial function.

6 Claims, No Drawings

(56) References Cited

OTHER PUBLICATIONS

Bradley R et al. "Coenzyme Q10 (CoQ10)" National Center for Complementary and Integrative Health, National Institute of Health, Mar. 2015: D489. www.nccih.nih.gov/D489 (6 pgs).
Bruce et al. "Improvements in Concentration, Working Memory, and Sustained Attention Following Consumption of a Natural Citicoline-Caffeine Beverage", Int J Food Sci Nutr Dec. 2014; 65(8):1003-1007 (11 pgs).
Bruce, Steven, "Improvements in Quantitative EEG Following Consumption of a Natural Citicoline-Enhanced Beverage", International Journal of Food Sciences and Nutrition, Jun. 2012; 63(4): 421-425 (8 pgs).
Canto et la., "The NAD+ Precursor Nicotinamide Riboside Enhances Oxidative Metabolism and Protects against High-Fat Diet-Induced Obesity" Cell Metabolism 15, 838-847, Jun. 6, 2012. (10 pgs).
Citicoline. Monograph, Thorne Research Group. Alt Med Rev 2008;13(1):50-57 (8 pgs).
Citicoline. Open Search PubChem. National Library of Medicine National Center for Biotechnology Information, National Institute of Health, updated Nov. 11, 2017 (43 pgs).
Clark, Wayne M. "Efficacy of citicoline as an acute stroke treatment" Expert Opinion Pharmacother. 2009, 10(5), pp. 839-846 (8 pgs).
Coenzyme Q10 Introduction Monograph, Alt. Med. Rev. vol. 12, No. 2, Jun. 2007: 159-175 (16 pgs).
Coenzyme Q10. PubChem Monograph. National Center for Biotechnology Information, National Library of Medicine, National Institute of Health, updated Nov. 11, 2017. www.pubchem.ncbi.nlm.nih.gov. (17 pgs).
Cohen, Deborah, "The truth about sports drinks". BMJ 2012; 345:e4737 (35 pgs).
Conant et al. "Therapeutic Applications of Citicoline for Stroke and Cognitive Dysfunction in the Elderly: A Review of the Literature", Alternative Medicine Review 2004; 9(1):17-31 (15 pgs).
Cundy T et al. Metabolic Bone Disease. Clinical Biochemistry: Metabolic and Clinical Aspects (3$^{rd}$ ed)2014, Elsevier Academic Press, Amsterdam; chapter 31:609-612 (72 pgs).
Das, Abhirup et al, "Impairment of an Endothelial NAD$^+$-H$_2$S Signaling Network Is a Reversible Cause of Vascular Aging" Cell 173, 74-89 Mar. 22, 2018 (37 pgs).
Dietary Guidelines for Americans 2015-2020, Eighth Edition, USDA DietaryGuidlines.gov USDA Publication #: Home and Garden Bulletin No. 232 (144 pgs).
Fargue et al., "Hydroxyproline Metabolism and Oxalate Synthesis in Primary Hyperoxaluria", JASN Jun. 2018 29(6) 1615-1623; https://doi.org/10.1681/ASN.2017040390.
Faust M et al. "Oral Rehabilitation Salts (ORS)" World Health Organization (WHO) (UNICEF). Production of the New ORS 1985. WHO Document Production Services, Geneva, Switzerland: 1-59 (123 pgs).
Fioravanti et al. "Citicoline (Cognizin®) in the Treatment of Cognitive Impairment" Clinical Interventions in Aging 2006; 1(3): 247-251 (5 pgs).
Food and Drug Administration (FDS) Report. Energy Drinks and Supplements: Investigations of Adverse Event Reports. US Food and Drug Administration,www.FDA.gov (3 pgs).
Fricker et al., "The Influence of Nicotinamide on Health and Disease in the Central Nervous System" International Journal of Tryptophan Research vol. 11: 1-11, 2018 (11 pgs).
Gareri et al., "The role of citicoline in cognitive impairment: pharmacological characteristics, possible advantages, and doubts for an old drug with new perspectives" Clinical Interventions in Aging, 2015; 10: 1421-1429 (14 pgs).
Givertz et al., "Role of Oxidative Stress in Heart Failure", Review of literature Sep. 2018 www.uptodate.com. (16 pgs).
Gollnick et al. "Significance of Skeletal Muscle Oxidative Enzyme Enhancement with Endurance Training". Clinical Physiology 1982;2(1):1-12 (12 pgs).

Gomes, Ana P. et al. "Declining NAD$^+$ Induces a Pseudohypoxic State Disrupting Nuclear-Mitochondrial Communication during Aging" Cell 155, 1624-1638, Dec. 19, 2013 (15 pgs).
Gong, Bing et al. "Nicotinamide riboside restores cognition through an upregulation of proliferator-activated receptor-$\gamma$ coactivator 1$\alpha$ regulated $\beta$-secretase 1 degradation and mitochondrial gene expression in Alzheimer's mouse model" NIH Public Access Author Manuscript, Neurobiol Aging Jun. 2013; 34(6): 1581-1588 (17 pgs).
Goody, Micelle et al., "A need for NAD+ in muscle development, homeostasis, and aging" Skeletal Muscle 2018, 8:9 (14 pgs).
Grieb P., "Citicoline: A Food That May Improve Your Memory", Medical Science Review 2015; 2: 67-72 (6 pgs).
Grieb P., "Neuroprotective Properties of Citicoline: Facts, Doubts and Unresolved Issues" CNS Drugs 2014; 28(3):185-193 (30 pgs).
Harris JL et al. "Sugary drink marketing to youth: Some progress but much room to improve" 2014. Rudd Center for Food Policy and Obesity. Nov. 2014 (167 pgs).
Harris JL et al. "Sugary Drinks FACTS in Brief" 2014. Rudd Center for Food Policy and Obesity. Nov. 2014. www.sugarydrinkfacts.org (4 pgs).
Harvard T.H. Chan School of Public Health, The Nutrition Source, "Healthy Beverage Guidelines", 2017. www.hsph.havard.edu/nutrition/source/healthy-drinks-full-story (7 pgs).
Hausmann, Ernest et al., "Conversion of Proline to Hydroxyproline and Its Incorporation into Collagen", The Journal of Biological Chemistry, vol. 236, No. 1, Jan. 1961 (5 pgs).
Heneghan C et al. Forty Years of Sports Performance Research and Little Insight Gained. BMJ 2012;345:e4797 (5 pgs).
Houtkooper et al., "The Secrect Life of NAD+: An Old Metabolite Controlling New Metabolite Signaling Pathways" Endocrine Reviews, Apr. 2010, 31(2): 194-223 (30 pgs).
Hydroxyproline, PubChem Monograph. National Center for Biotechnology Information. National Library of Medicine, National Institute of Health, updated Nov. 11, 2017. www.pubchem.ncbi.nlm.nih.gov. (8 pgs).
Institute of Medicine. 2005. Dietary Reference Intakes for Water, Potassium, Sodium, Chloride, and Sulfate. Washington, DC: The National Academies Press. doi: 10.17226/10925 (43 pgs).
Jacobs RA et al. "Improvements in Exercise Performance with High-Intensity Interval Training Coincide with an Increase in Skeletal Muscle Mitochondria Content and Function". J Appl Physiol 2013;115(6):785-793 (15 pgs).
Jafari, Mehdi, "Coenzyme Q10 in the treatment of heart failure: A systematic review of systematic reviews", Indian Heart Journal 70S (2018) S111-S117 (8 pgs).
Joy of Life—Best for Life, "Ultra + Multivitamin 500 mL", https://web.archive.org/web/20181028013627/http://www.joyoflife.ee/et/a/swedish-nutra-ultra-multivitamin, Oct. 28, 2018, 2 pages).
Khan et al., "Modeling of hyperoxaluric calcium oxalate nephrolithiasis: experimental induction of hyperoxalura by hydroxyl-L-proline", Kidney Int Sep. 2006: 70(5): 914-23.
Kim et al., "Hydroxyprolinemia: Comparsion of a patient and her unaffected twin sister", From the Division of Genetics, Children's Hospital, and the Departments of Pediatrics and Psychiatry, pp. 437-441.
Knight et al., "Hydroxyproline ingestion and urinary oxalate and glycolate excretion", Kidney Int Dec. 2006: 70(11): 1929-34.
Kumanyika S et al. National Academies of Science, Engineering and Medicine Consensus Study Report, 2017: Principles of Developing Dietary Reference Intakes (DRI) Based on Chronic Disease. National Academies Press, 2017Washington D.C. www:doi.org/10.17226/24828 (89 pgs).
Langlois et al. "The Epidemiology and Impact of Traumatic Brain Injury: A Brief Overview". J Head Trauma Rehabil 2006; vol. 21, No. 5, 375-378 (4 pgs).
Lee et al. "Prion-like Mechanism in Amoyotrophic Lateral Sclerosis: are Protien Aggregates the Key?" Ezperimental Neurobiology, Mar. 2015: 24(1): 1-7 (7 pgs).
Lozano FR. Efficacy and Safety of Oral CDP-Choline. Drug Surveillance Study in 2817 Cases Arzneimittelforschung 1983;33:1073-1080, abstract only (1 pg).
Lozano R. "CDP-Choline in the Treatment of Cranio-Encephalic Traumata" Journal of Neuroslogical Sciences 1991; 103, Suppl:S43-S47 (5 pgs).

(56) References Cited

OTHER PUBLICATIONS

Magni, G. et al. "Enzymology and NAD+ homeostasis in man" *CMLS Cellular and Molecular Life Sciences* 61 (2004) 19-34 (16 pgs).
Maughan RJ et al. "Sports Drinks: Basic Science and Practical Aspects." CRC Press, Taylor & Francis, Inc., Philadelphia 2000;1:1-304 (28 pgs).
McGlade E et al. "Improved Attentional Performance Following Citicoline Administration in Healthy Adult Women", *Food and Nutrition Science* 2012; 3(6): 769-773 (8 pgs).
McGlade et al. "The Effect of Citicoline Supplementation on Motor Speed and Attention in Adolescent Males". *Journal of Attention Disorders*, 2015; pp. 1-14 (14 pgs).
McKee et al. "Chronic Traumatic Encephalopathy in Athletes: Progressive Tauopathy After Repetitive Head Injury", *J Neuropathol Exp Neurol* 2009; 68(7): 709-735 (27 pgs).
Milliner et al., "Primary Hyperoxaluria Type 1" GeneReviews [Internet], Jun. 19, 2002.
Mortensen et al. "The Effect of Coenzyme Q10 on Morbidity and Mortality in Chronic Heart Failure: Results From Q-SYMBIO: A randomized Double-Blind Trial". *JACC Heart Failure* 2014; 2: 641-649 (10 pgs).
Nicolson, Garth L, "Mitochondrial Dysfunction and Chronic Disease: Treatment With Natural Supplements", *Alternative Therapies*, vol. 20, Suppl. 1, 2014, pp. 18-25 (8 pgs).
NIH Gard, Hydroxyprolinemia, Summary updated Aug. 10, 2011, https://rarediseases/info/nih.gov/dieseases/10717/hydroxyprolinemia.
Nonaka et al., "Prion-like Properties of Pathological TDP-43 Aggregates from Diseased Brains" *Cell Reports*, 4, Jul. 11, 2013, 124-134 (11 pgs).
Pascual-Leon, Alvaro et al., "Chronic Traumatic Encephalopathy and Age of First Exposure to American-style Football" Accepted Article (5 pgs).
Percival, M., "Nutritional Support for Connective Tissue Repair and Healing" *Clinical Nutrition Insights*, 1997 Rev. 6-98 (4 pgs).
Primary Hyperoxaluria, description information, 4 pages.
Popkin et al. "A New Proposed Guidance System for Beverage Consumption in the United States". *American Journal of Clinical Nutrition*, 2006; 83: 529-542 (24 pgs).
Prockop et al. "Relationship of Hydroxyproline Excretion in Urine to Collagen Metabolism: Biochemistry and Clinical Application", *Annals of Internal Medicine*, 1967; vol. 66, No. 1243-1266 (24 pgs).
Saini, Janmeet et al., "Nicotinamide Ameliorates Disease Phenotypes in a Human iPSC Model of Age-Related Macular Degeneration" *Cell Stem Cell* 20, 1-13, May 2017 (21 pg).
Sarter B. Coenzyme Q10 and Cardiovascular Disease: A Review. J Cardiovas Nursing 2002;16(4):9-20 (12 pgs).
Sauve, Anthony A. "NAD+ and Vitamin $B_3$: From Metabolism to Therapies" *The Journal of Pharmacology and Experimental Therapeutics* Mar. 2008, 324 (3) 883-893 (25 pgs).
Secades, J. "Pharmacological and Clinical Review" 2010 Update. *Review of Neurology* 2011; 2, Suppl 2: S1-S48 (1 pg).
Secades, Julio J. et al., "Citicoline for Acute Ischemic Stroke: A Systematic Review and Formal Meta-analysis of Randomized, Double-Blind, and Placebo-Controlled Trials" *J of Stroke and Cerebrovascular Diseases* May 2016 (17 pgs).
Seifert et al., "Health Effects of Energy Drinks on Children, Adolescents, and Young Adults", *Pediatrics* vol. 127, No. 3, Mar. 2011, p. 511-528 (20 pgs).
Siliveri et al. "Citicoline Enhances Frontal Lobe Bioenergetics as Measured by Phosphorus Magnetic Resonance Spectroscopy" *NMR Biomed* 2008; 21(10):1066-1075 (14 pgs).
Skripuletz et al. "Pivotal Role of Choline Metabolites in Remyelination", *Brain, Journal of Neurology* 2015; 138: 398-413 (24 pgs).
Skripuletz et al. "The Choline Pathway as a Strategy to Promote Central Nervous System (CNS) Remyelination", *Neural Regeneration Research* Sep. 2015; 10(9): 1369-1370 (6 pgs).
Staufner et al., "Genetic cause and prevalence of hydroxyprolinemina", J. Inherit Metab Dis, Feb. 10, 2016 (8 pages).

Suzuki, Eri et la., "Protective effect of nicotinamide against poly(ADP-ribose) polymerase-1-mediated astrocyte death depends on its transporter-mediated uptake" *Life Sciences* 86 (2010) 676-682 (7 pgs).
Swithers SE, "Dangerous Effects of Artificial Sweeteners on Your Health" www.medicaldaily.com/4-dangerous-effects-of-artificial-sweeteners-on-your-health (3 pgs).
Szoka et al., "Cellular and Molecular Life Sciences" Cellular and Molecular Life Sciences, Oct. 2019 (6 Suppl): 1-8.
Tan HB et al. "Citicoline (CDP-Choline) for Traumatic Brain Injury (Protocol)", Cochrane Database of Systemic Reviews 2014; Issue 8 Article No. CDO-11217) OI:10.1002/14651858.CDO11217 (7 pgs).
Trammel, Samuel A.J., "Novel NAD+ metabolomic technologies and their applications to Nicotinamide Riboside interventions". PhD thesis, University of Iowa, 2016 (208 pgs).
Vanderthommen et al. "Electrical Stimulation as a Modality to Improve Performance of the Neuromuscular System". *Exercise and Sport Science Review*, 2007;35(4):180-185 (6 pgs).
VKM Report 2016:60; Risk Assessment of Other Substances: L-Proline, 206:60 (1 pg).
Vrentas, J. "Medical Care: Brett Farve and other NFL stars are backing the efforts of pharmaceutical companies to develop drugs that would treat football's concussion scourge" Sports Illustrated Nov. 2017;18-19 (3 pgs).
Welch, A., CBS News "Sugary drinks lead to thousands of deaths, study finds", *CBS Interactive Inc.*, Jun. 30, 2015 (4 pgs).
Wu, "Important roles of dietary taurine, creatine, carnosince, anserine and 4-hydroxyproline in human nutrition and health", Amino Acids, vol. 52, pp. 329-360 (2020).
Wu et al., "Proline and hydroxyproline metabolism: implications for animal and human nutrition", NCBI, Published online Aug. 10, 2010 (15 pages).
Yang et al., "Nutrient-Sensitive Mitochondrial NAD+ Levels Dictate Cell Survival" *Cell* 130, 1095-1107, Sep. 21, 2007 (13 pgs).
Ying, Weihai, "NAD+/NADH and NADP+/NADPH in Cellular Functions and Cell Death: Regulation and Biological Consequences" *Antioxidants & Redox Signaling* vol. 10, No. 2, 2008 (28 pgs).
Ying, Weihai, "Therapeutic potential of NAD+ for neurological diseases", *Future Neurol.* (2007) 2(2), 129-132 (4 pgs).
Yoshino et al., "Nicotinamide Mononucleotide, a Key NAD+ Intermediate, Treats the Pathophysiology of Diet- and Age-Induced Diabetes in Mice" *Cell Metabolism* 14, 528-536, Oct. 5, 2011 (9 pgs).
Yoshino, Jun et al., "NAD+ Intermediates: The Biology and Therapeutic Potential of NMN and NR" *Cell Metabolism* vol. 26, Mar. 7, 2018 (16 pgs).
Zafonte et al. "The Citicoline Brain Injury Treatment (COBRIT) Trial: Design and Methods". *Journal of Neurotrauma* 2009; 26(12): 2207-2216 (10 pgs).
Zeisel, Steven H., "Choline: An Essential Nutrient for Public Health" *Nutr. Rev.* Nov. 2009. 61(11): 615-623 (8 pgs).
Zhou, Minghai et al., "Neuronal death induced by misfolded prion protein is due to NAD+ depletion and can be relieved in vitro and in vivo by NAD+ replenishment", Brain, *J of Neurology* 2015: 138; 992-1008 (26 pgs).
International Search Report and Written Opinion issued in related PCT International Patent Application Serial No. PCT/US2019/062257, dated Mar. 25, 2020 (7 pages).
International Preliminary Report on Patentability issued in related PCT International Patent Application Serial No. PCT/US2019/062257, dated May 25, 2021 (5 pages).
Office Action issued in U.S. Appl. No. 15/913,619, dated Apr. 2, 2019 (12 pgs).
Office Action issued in U.S. Appl. No. 15/913,619, dated Jul. 11, 2019 (33 pgs).
Office Action issued in U.S. Appl. No. 15/913,619, dated Nov. 7, 2019 (16 pgs).
Office Action issued in U.S. Appl. No. 15/913,619, dated Apr. 16, 2020 (17 pgs).
Office Action issued in U.S. Appl. No. 15/913,619, dated Oct. 5, 2020 (35 pgs).
Office Action issued in U.S. Appl. No. 16/195,425, dated Jun. 13, 2019 (17 pgs).

(56) References Cited

OTHER PUBLICATIONS

Office Action issued in U.S. Appl. No. 16/195,425, dated Jul. 25, 2019 (17 pgs).
Office Action issued in U.S. Appl. No. 16/195,425, dated Nov. 7, 2019 (6 pgs).
Office Action issued in U.S. Appl. No. 16/195,425, dated Feb. 6, 2020 (17 pgs).

* cited by examiner

BIOLOGIC ENHANCEMENT FORMULATION

CROSS REFERENCE TO RELATED APPLICATIONS

This application is a continuation-in-part of and claims priority to U.S. patent application Ser. No. 17/244,814, filed Apr. 29, 2021, which is a continuation-in-part of and claims priority to PCT International Patent Application Serial No. PCT/US2019/062257, Filed Nov. 19, 2019, which claims priority to U.S. patent application Ser. No. 16/195,425, filed Nov. 19, 2018, which is a continuation-in-part to U.S. application Ser. No. 15/913,619, filed Mar. 6, 2018, which claims priority from U.S. Provisional Application Ser. No. 62/469,376, filed Mar. 9, 2017, the entire disclosures of which are incorporated herein by reference.

TECHNICAL FIELD OF THE INVENTION

The present invention refers to an all-natural formulation that provides scientific, evidence-based, central nervous system (CNS) benefits, cardiovascular system (CVS) benefits, and connective tissue system benefits (CTS) benefits, gut microflora ("Gut Biome") benefits, anti-obesity benefits, anti-diabetic benefits, anti-liver cirrhosis benefits, anti-microbial benefits, anti-oxidative stress benefits, and systemic anti-inflammatory benefits. This novel biologic-enhancing formulation preferably is in the form of beverage, or powder concentrate that can be added to a beverage, and will be described in connection with such forms, although other forms are contemplated. The formulation as a beverage, in addition to providing rapid water and homeostatic rebalance, provides the potential to maximize human brain/neurologic cell capacity for repair and accelerated return to normal function following head injury (Traumatic Brain Injury (TBI)), concussion and/or post-concussion syndromes, stroke, ischemic brain injury, and has the potential to reduce symptoms and repair the damage from neurodegenerative disorders. The formulation also provides relief for patients suffering from infections caused by spirochetes, such as Lyme Disease and Syphilis. Accelerated repair, regeneration and maintenance of neuronal, skeletal muscle, cardiac muscle and connective tissue is enhanced by providing specific biologic precursors, in addition to gut biome enhancement, systemic anti-microbial, anti-oxidative stress and systemic anti-inflammatory mediators. The formulation of the present invention contains zero to very low amounts of calories that do not contribute to weight gain, maintenance of obesity, transient increases in blood glucose or blood insulin levels.

BACKGROUND OF THE INVENTION

The most popular category of so called "healthy" beverages that are promoted for hydration include sports drinks. Sport drinks are beverages with the stated purpose of replacing water, electrolytes, and increasing energy, in the form of sugar, before, during, and after training or athletic competition.[1,2]

Available on the market today are a myriad of energy, nutrient, and vitamin replacement drinks, as well as many products which claim increased energy ingredient(s) for improved performance. The current spectrum of commercially available oral hydration sports/energy drinks can be categorized into three general types: (1) electrolyte containing, (2) vitamin containing, and (3) stimulant substance containing. The stimulant substances often are in the form of sugar, caffeine, ginseng, guarana or ephedra.[1,2,5]

Currently, sport drink oral hydration manufacturers attempt to mimic the World Health Organization's (WHO's), oral rehydration therapies and guidelines. The WHO's oral rehydration therapy recommendations are intended as treatment for a disease-based-model where electrolytes and fluids are depleted as a direct result of life-threatening gastrointestinal diseases.[4] Prior to our invention, there has been no distinction to increase a specific cerebral neuronal nutrient in any hydration setting, including a disease population, a sedentary population, a normal population, or an "in-training" athletic population.

One bottle (609 grams) of sports drink typically contains 10% of an RDA 2000 calorie diet of sodium 13% of an RDA 2000 calorie diet of carbohydrates in the form of sugar. This exceeds the amount of sodium lost and the amount of calories burned in an hour of average athletic activity that this class of beverage is frequently consumed for.[1,4] The reality is that when hydrating due to thirst, sports drinks or beverages, especially when consumed multiple times per hour, to replace lost water and electrolytes, are not healthy due to the load of unnecessary electrolytes and excess calories.[2,5] While exercise training may require pre-exercise, exercise and post-exercise fluid, electrolyte and carbohydrate replacement, as well as post-exercise repletion of salts and carbohydrates, sports drinks provide an excess of electrolytes and sugar.[3,5]

Researchers in exercise science have concluded that muscle tissue can improve its response to training stimulus not only by increasing enzyme and mitochondrial concentrations in muscle cells and/or increasing capillary density,[6] but also by increasing neural stimulation and demand.[7] The first two processes require proteins, vitamins and mineral co-factors to activate enzymes and mediate cell membrane integrity.[8] These processes can be enhanced by many of the currently available sports and energy drink products.[9] The latter processes of increased neural stimulation and demand, include: (1) increased muscle fiber adaptation throughout the nervous system, (2) increased and more effective neural recruitment, (3) increased neural firing rate, and (4) improved neural firing synchronicity.[10] There has been no prior selective support for these processes until our all-natural biologic-enhancing beverage invention.

Moreover, currently available products which contain stimulant substances, can induce deleterious cardiac, vascular and endocrine complications.[2,11]

There is thus a current need for an improved and healthy hydration drink which can support the specific neurophysiologic demands of athletic training for fitness and endurance, general fitness in the non-athlete population, provide pre and post brain injury and degenerative disorder neuronal repair and support, sustain and maintain pre and post cardiovascular cellular activity, and pre and post activity connective tissue integrity, to enhance repair and maintenance for optimal function.[12,13]

SUMMARY OF THE INVENTION

The present invention provides an ingestible formulation, preferably in the form of a beverage or power concentrate that can be added to a beverage, which distinguishes itself from current hydration products such as sport drinks, by addressing the physiological requirement for hydration without the need for overconsumption of sodium, potassium, chloride and sugar derived calories.[14,46] This invention provides substrates for enhanced repair and maintenance of the central nervous system with Citicoline[15, 16, 22-26, 74] and a Nicotinamide Adenine Dinucleotide (NAD+) precursor,[43, 51-58, 62-70] the cardiovascular system with Coenzyme Q10(CoQ10)[17-19, 44, 77] and NAD+ precursor[49, 56, 62, 63] and the connective tissue system with hydroxyproline[19] and NAD+ precursor.[43, 55, 58, 63, 69] When in the form of a beverage, electrolytes are incorporated for palatability rather than as a replacement for electrolyte loss. Natural non-caloric sweeteners are incorporated for palatability, rather than sugar as a source of energy repletion, and to reduce reactive pancreatic secretion of insulin to an oral glycemic load. Citicoline and NAD+ precursor selectively provide nutritional benefit for central nervous system cells (neurons) for maintenance of homeostatic physiology and the potential for enhanced repair and regeneration, in a preventative paradigm, given the possibility of CNS/Head injury (TBI)[20, 21, 60], or onset of CNS degenerative disorders.[54, 57] CoQ10[17, 18, 19, 37] and NAD+ precursor[49, 62, 63] selectively provide nutritional benefit for the heart muscle and blood vessels for maintenance of homeostatic physiology, resistance to oxidative stress, and enhanced potential for repair, in a preventative paradigm, given the possibility of CVS stress and injury.[17, 18, 19, 49, 62, 67] Hydroxyproline selectively provides nutritional benefit for the integument for maintenance of homeostatic physiology and potential repair, in a preventative paradigm, given the possibility of connective tissue injury.[9, 38, 39, 43, 62, 63]

In one aspect of the invention there is provided a formulation comprising Citicoline, CoQ10, hydroxyproline, and at least one niacinamide adenine dinucleotide (NAD+) precursor. The formulation preferably is in powder concentrate, dissolved or suspended in a liquid carrier, preferably water, and optionally includes a hydration improving substance which comprises at least one of an electrolyte, a carbohydrate and a phospholipid.

In one embodiment of the invention, the hydration improving substance comprises at least one of sodium, potassium, magnesium, calcium, and chloride, and a "zero calorie" or "low calorie" natural sweetener, in the form of Allulose, Stevia or monk fruit sweetener. Allulose is a naturally occurring sugar found in figs, raisins, wheat, maple syrup and molasses. It is sweet like sucrose, but without some of sucrose's downsides. Stevia is a sugar substitute made from the leaves of garden flowers such as asters and chrysanthemums. It is about 100 to 300 times sweeter than sucrose. Monk fruit sweetener is made from an extract derived from dried monk fruit. The extract is about 150-250 times sweeter than sucrose.

The formulation of the present invention preferably is in the form of an isotonic beverage, a hypertonic beverage, or a hypotonic beverage, and preferably is an osmolality in the range of 10-999 mmol/kg and has a pH in the range of 2.5-9.5.

In one embodiment of the invention, the formulation further comprises at least one additional ingredient selected from the group consisting of carbonation, a sweetener, a flavorant, an acidulant, a colorant, a vitamin, a mineral, an antioxidant, a preservative, an emulsifier, a thickening agent, a clouding agent, and combinations of any of them. In such embodiment, the flavorant preferably comprises a natural cola flavor or natural fruit flavor selected from the group consisting of cola, orange, mandarin orange, blood orange, tangerine, clementine, grapefruit, lemon, lime, tangelo, apple, grape, pear, peach, nectarine, apricot, plum, prune, pomegranate, blackberry, blueberry, raspberry, strawberry, cherry, cranberry, currant, gooseberry, boysenberry, huckleberry, mulberry, date, pineapple, banana, mango, papaya, lychee, passion fruit, coconut, guava, kiwi, watermelon, cantaloupe, honeydew melon, hibiscus, and other natural fruits or derivative combinations thereof, and the acidulant preferably is selected from the group consisting of citric acid, ascorbic acid, malic acid, lactic acid, tartaric acid, cinnamic acid, fumaric acid, maleic acid, adipic acid, glutaric acid, succinic acid, and/or other natural acidulants or derivative combinations thereof.

The formulation of the present invention may be in the form of a frozen or non-frozen liquid, a semi-solid liquid or gel, slush, popsicle, or gummy, or in the form of a liquid concentrate, or a gel concentrate, or a solid form concentrate such as a powder, beads or tablet concentrate.

In another embodiment of the present invention, the formulation is in a form of a powder adapted to be hydrated for reconstituting a beverage, or in a dry form as a tablet or capsule, or as gel, a food bar, a baked good, a smoothie, or other foodstuff or edible preparation.

In a preferred embodiment of the present invention, the Citicoline is in a form of the B-vitamin choline, which acts as a choline donor and an intermediate in the biosynthesis of phospholipids and acetylcholine, The present invention also provides a method, with an NAD+ precursor, such as Nictotinamide (Vitamin B3, Niacin), Nicotinamide Riboside (NR), Nicotinamide Mono-Nucleotide (NMN), the reduced form of Nicotinamide Adenine Dinucleotide (NADH), Triphosphopyrididine Nucleotide (TPN), and the reduced form of Nicotinamide Adenine Dinucleotide Phosphate (NADPH),[43, 55, 58, 62, 73] for potentially enhancing the health of an individual by reducing symptoms due to neurodegenerative disorders. Animal studies utilizing the NAD+ precursors, Nicotinamide Riboside (NR) and Nicotinamide Mono Nucleotide (NMN), demonstrate significant reduction of neurodegenerative symptoms for Ischemic Brain Damage, Traumatic Brian Injury (TBI), Huntington's Disease (HD), Amyotrophic Lateral Sclerosis (ALS), Parkinson's Disease (PD), Alzheimer's Disease (AD), vascular aging, Dementia, and anti-aging effects related to NAD+ depletion[43, 49, 51-54, 56-59, 75, 76] In another embodiment, the disease is an infectious disease caused by spirochetes, such as Lyme Disease or Syphilis. The present invention provides for the method, with one of the natural "zero-calorie" or "low calorie" sweeteners, in the form of Allulose, Stevia extract and/or monk fruit extract, to provide optimal sweetness, with low glycemic index, anti-diabetic/anti-obesity benefits, anti-fatty-liver, anti-oxidative stress and anti-inflammatory benefits, while supporting a heathy GI biome. In the disclosed methods, a formulation as described herein is administered to an individual. The formulation may be administered as a liquid or suspension in a liquid carrier, preferably water.

DETAILED DESCRIPTION OF THE INVENTION

The present invention provides a new, unique, and novel formulation which comprises the neuronal-nutrients citicoline and NAD+ precursor, the cardiovascular nutrients CoQ10, and NAD+ precursor, and the connective tissue nutrients hydroxyproline and NAD+ precursor. The formulation, when in the form of a beverage, can be ingested before, during and after physical exercise to replenish general body nutrient losses. Unlike currently available sports/energy drinks, the formulation of the present invention optimizes the neurologic milieu in which brain cells modulate muscle cell responses during athletic and endurance training, optimize the cardiovascular milieu in which cells of the cardiovascular system provide circulatory support for nutrients, oxygenation, and removal of tissue metabolites, and optimize the cells of the connective tissue system for repair and maintenance of the integument by the synthesis of collagen. In the advent of a CNS neuronal injury, the formulation of the present invention provides neurologic-protection. In addition, the formulation of the present invention increases alertness and energy for improved exercise performance, enhances CNS neuron to muscle adaptation and modulates the effects of body and neuronal physiologic stress. Its unique and novel substituents, Citicoline,[23, 24, 28-30, 32, 33], NAD+ precursor[43, 58, 61, 62, 69, 71, 72], and CoQ10[17-19, 37, 44, 77] enhance alertness, learning speed, sustained attention, memory and reaction time to improve an athlete's performance.[28, 30, 32, 63, 69, 72] The formulation of the present invention also prophylactically renders neuronal protection in the possible event of a CNS micro or macro trauma.[20-22, 25, 27, 31, 34-36, 41, 49, 51-54] The addition of Citicoline and NAD+ precursor to the biologic-enhancing formulation of the present invention in its aqueous form, does not alter its effectiveness, stability or half-life. Citicoline and NAD+ precursors are believed to have no known adverse effects, nor do they have negative effects on the beverage's palatability, shelf-life or flavor.

A formulation in accordance with the present invention in the form of a hydrating beverage comprises: between about 0.01 and 0.05% by weight Citicoline, preferably 0.02-0.03% by weight Citicoline, more preferably 0.03-0.04% by weight Citicoline, even more preferably 0.04-0.05% by weight Citicoline;
  0.01-0.05% by weight NAD+ precursor, Nicotinamide Riboside (NR), preferably 0.02-0.03% by weight NAD+ precursor (NR), more preferably, 0.03-0.04% by weight NAD+ precursor (NR), even more preferably 0.04-0.05% by weight NAD+ precursor (NR);
  0.01-0.05% by weight CoQ10, preferably 0.02-0.03% by weight CoQ10, more preferably 0.03-0.04% by weight CoQ10, even more preferably 0.04-0.05% by weight CoQ10;
  0.01-0.05% by weight hydroxyproline, preferably 0.02-0.03% by weight hydroxyproline, more preferably 0.03-0.04% by weight hydroxyproline, even more preferably 0.04-0.05% by weight hydroxyproline; and
  water.

The addition of the brain cell micronutrients, Citicoline and NAD+ precursor, to the formulation of the present invention affords an increased potential for human brain/nerve cell repair and maintenance beyond the formulation's capacity to rehydrate and reconstitute electrolytes after acute depletion through metabolism, respiration, perspiration and disease-related fluid loss. The formulation of the present invention replenishes and maintains the optimum neurochemical balance for healthy brain/nerve cell function[20, 23-26, 29, 30, 33, 41-44, 54-58, 61, 62, 68, 69, 71, 72, 75-77]

When provided as a beverage, the formulation modulates the body's physiologic stress from athletic training at a general fitness level, at an endurance-athlete level, and at the CNS neurophysiologic level.[23, 24, 28-30, 32, 55] Citicoline has been shown to improve neuronal response to injury via multiple molecular mechanisms as extensively documented in numerous studies, including animal models, cellular in-vitro models, human in vivo ischemia/stroke head injury models and human in vivo head trauma models, with on-going studies on aging, learning, improved memory, dementia, dyskinesia, Parkinson's Disease and other neurological disorders.[21, 23, 25] Citicoline is the precursor substituent for the synthesis of phosphatidylcholine, a major component of nerve and cell membranes.[16, 41] Citicoline and its hydrolysis products further produce neuronal proteins, nucleic acids and acetylcholine which all enhance the nerve cell's response to wound healing.[25, 40-42]

Additionally, while not wishing to be bound by theory, the intestinal hydrolysis of Citicoline to the molecular products of cytidine and choline is believed to provide substituents for neuronal (brain cell) membrane repair via phospholipid generation and inhibition of cell damage, manifest as improved neuronal cell membrane integrity, decreased edema, and improved intracellular enzyme response to damage.[15, 16, 20, 21] The Citicoline also may be provided in a form of the B-vitamin choline, which acts as a choline donor and intermediate in the biosynthesis of phospholipids and acetylcholine.[25, 42]

Moreover, Citicoline, at the molecular level, reduces the cerebral production of free-radicals in neuronal cells and improves cerebral blood flow selectively to brain damaged areas.[15, 16, 20, 21, 22, 23, 25, 29, 29, 30, 40, 41, 54]

Additionally, Citicoline is readily and preferentially taken up by brain cells via osmosis for neuronal cell membrane re-genesis via phospho-lipid synthesis, inhibition of phospholipid degradation, with enhanced cellular repair responses and overall improved neuronal function in a traumatized, brain-injured milieu.[20-22, 26, 27, 34, 35, 53, 74]

Furthermore, Citicoline also is utilized for enhancement of normal functioning at baseline in non-traumatized persons, to include such functions as mental-alertness, memory, learning speed and has been further investigated utilizing EEG assessment criteria with positive placebo-controlled findings[16, 24, 29, 31, 32, 33]

And, Citicoline as a natural and normal cerebral-function enhancer improves neurocognitive functioning as evident by performance and EEG criteria.[33] Performance parameters included attention, sustained attention, concentration and reaction time. All performance parameters significantly improved with administration of a Citicoline-caffeine combination.[28]

Citicoline, has been scientifically proven, through evidence based research, to improve alertness, learning speed, sustained attention, memory and reaction time for the optimization of performance.[16] In response to recent attention given to brain neuronal micro-trauma, concussion and other CNS (central nervous system) injuries that commonly occur during sports-related activities,[34, 35, 36] the formulation of the present invention, which includes Citicoline, provides essential physiologic and neurophysiologic nutrients to the body and brain, prior to injury, to improve the human brain cell's inherent capacity to repair, return to, and maintain normal function.[15, 16, 20]

The addition of NAD+ precursors is believed to enhance the central nervous system,[54-58] the cardiovascular system,[58, 62, 67, 70, 71, 72] and the connective tissue system[63, 67, 69, 71], by enhancing cellular energy metabolism, mitochondrial function, calcium homeostasis and reducing cell aging by decreasing oxidative cell death.[55, 58, 71, 72] NAD+, the oxidized form, and NADH, the reduced form, are crucial for energy metabolism in the mitochondria of all cells.[56, 58, 62-73] NAD+/NADH participate in energy producing oxidation-reduction (redox) reactions in the tricarboxylic acid (TCA) cycle, within the mitochondria all human cells. NAD+/NADH are involved in an exchange of electrons, under the control of catalytic enzymes called oxidoreductases, or dehydrogenases and reductases. This exchange of electrons yields energy, which is used to create Adenosine Triphosphate (ATP). ATP molecules power all cells for each specific cellular function[54, 55, 58, 63] NAD+ is not consumed in the TCA cycle but is consumed by other reactions within the cells. Post-translational reactions such as deacetylation and ADP-ribosylation, necessitate replenishment of cellular NAD+ stores.[63-65] NAD+ deficiencies can be related to the lack of Vitamin B3 consumption, or from neurodegenerative disorders such as ALS and PD, which are caused by defects in the messenger RNA genetic templates, needed for production of the catalytic oxidoreductase (dehydrogenase and reductase) enzymes. These vital enzymes control NAD+/NADH electron transfer and energy production. Lack of energy production from redox reactions leads to mitochondrial dysfunction and death. Mitochondrial decline disrupts cellular homeostasis, leading to cell death and subsequent organismal failure.[64-69, 71, 72] Supplementation of NAD+ by consumption of NAD+ precursors, such as NADH, NR, NMN and NADPH has been demonstrated in animal studies, to ameliorate many systemic degenerative symptoms related to NAD+ deficiencies.[54, 55, 58, 62, 75-77]

The addition CoQ10 is believed to protect the cardiovascular system by reducing the oxidation of LDL cholesterol, assist in maintaining the health of blood vessels, protect against clot and plaque rupture, and support optimal functioning of cardiac tissue.[17, 18, 37]

The addition of hydroxyproline is believed to provide precursor molecules for the synthesis of new connective tissue for maintenance of normal connective tissue function and regeneration of collagen for repair of connective tissue necessitated by athletic endeavors, daily activities, and injury.[19, 38, 39]

Specifically, the formulation of the present invention provides, a novel and unique hydration beverage or foodstuff, which contains a proprietary formulation of the neuronal micronutrients, Citicoline, in combination with conventional nutritional substances supporting the CNS. CVS, and CTS to include a mixture of any or all of the following: citric acid, L-citrulline, sphingolipids, L-tyrosine, L-theanine, resveratrol, choline, DMAE bitartrate, inositol, huperzine A, vinpocetine, guarana, boron, essential fatty acids, natural sweeteners, ascorbic acid (vitamin C), citric acid, tocopherol (vitamin E), Beta-carotene (pro-vitamin of vitamin A), pyridoxine (vitamin B6), thiamine (vitamin B1), riboflavin (vitamin B2), niacin and/or niacinamide (vitamin B3), co-enzyme niacinamide adenine dinucleotide (NAD+) and/or precursors thereof (e.g., niacinamide, niacinamide mononucleotide (NMN), and niacinamide adenine dinucleotide hydride (NADH)), cyanocobalamin (vitamin B12), folacin (folic acid), biotin, co-enzyme Q10, hydroxyproline, hyaluronic acid, ceramide, chondroitin, hydroxylysine, N-acetyl cysteine, copper, magnesium, manganese, selenium, zinc, chromium, essential and nonessential amino acids, any and all of their parent compounds and/or their derivatives and any other nutritionals that are determined to be biologically beneficial for optimization of central nervous system cellular activity and cognition, optimization of cardiovascular cellular activity and function, and optimization of connective tissue system cellular activity and function.

As previously mentioned, the disclosed formulations may include one or more NAD+ precursors. Niacinamide (Vitamin B3), also called nicotinamide, is the precursor to nicotinamide adenine dinucleotide (otherwise referred to as niacinamide adenine dinucleotide or NAD+). Nicotinamide Riboside (NR) and Nicotinamide Mononucleotide (NMN) and Nicotinamide Adenine Dinucleotide Phosphate (NADPH) are also NAD+ precursors. Without an abundance of mitochondrial NAD+, which is a potent free radical scavenger, the neuronal mitochondria are killed from free radical toxicity, the neurons die and the toxic intracellular components, including the defective messenger RNA, also referred to as PRIONs, spread to adjacent neurons, like an infection, as the dead cells disintegrate. This process slowly destroys large regions of the brain and eventually kills the host[54, 75, 76]

Without wishing to be bound by theory, it is believed that NAD+ precursors may, in some cases, provide health benefits. For example, NAD+ precursors may be particularly useful in improving symptoms of Amyotrophic Lateral Sclerosis (ALS).[48, 57] It has been suggested that NAD+ (and precursors thereof) may contribute to reversal and stabilization of neurodegenerative disorders, such as Dementia and Alzheimer's Disease. NAD+ therapy also appears to slow down aging.[48, 56, 57, 58] Animal studies using NAD+ in which animals ingest an NAD+ precursor, such as niacinamide, NMN, NR, or NADH, have demonstrated significant elevation in mitochondrial NAD+, with substantial reduction in symptoms of neurodegenerative disease.[48, 49, 57, 65, 75, 76]

In select embodiments, the disclosed formulations include a niacinamide adenine dinucleotide (NAD+) precursor, such as niacinamide, nicotinamide mononucleotide (NMN), nicotinamide riboside (NR) or nicotinamide adenine dinucleotide hydride (NADH). The NAD+ precursor may be present in any desired weight percent. For example, the disclosed formulations may, in some embodiments, include between about 0.01 and 0.05% by weight NAD+ precursor, preferably 0.02-0.03% by weight NAD+ precursor, more preferably 0.03-0.04% by weight NAD+ precursor, even more preferably 0.04-0.05% by weight NAD+ precursor. Any suitable amount of NAD+ precursor may be used in the disclosed formulations, and it has been found that the presence of NAD+ precursor (even in a relatively high weight percentage) does not cause undesirable effects in taste or side effects.

In addition to a beverage, the same ingredients can be formulated into frozen and non-frozen liquids, semi-solid liquids, or gel, slush or gummy, popsicles and further, can be incorporated into a powder concentrate or solid form tablet or lozenge, comprising any and all processed foodstuffs. Thus, the present invention is intended to cover all forms of ingestible products incorporating Citicoline, NAD+ precursor, CoQ10 and hydroxyproline, in combination, in a frozen or non-frozen solid state, or in the form of a powder that can be hydrated for reconstituting a beverage, or formed in a dry form into a tablet, capsule or gel, a food bars, baked good, smoothie, or other foodstuff or edible preparation.

The specific nutrient and food supplements unique to our beverage, Citicoline, NAD+ precursor, CoQ10, and hydroxyproline have been scientifically proven to promote specific central nervous system benefits, specific cardiovascular system benefits, and specific connective tissue benefits respectively. Citicoline,[40, 41, 42] NAD+ precursors,[56, 58] CoQ10,[43, 44] and hydroxyproline[45] have not been reported to produce significant adverse effects or toxicities, and as food or food supplements, have been categorized by the FDA as "generally recognized as safe".

In contrast to stimulant substances, Citicoline has demonstrated properties of central neuron repair and protection in laboratory and animal models. Citicoline has further been identified as a CNS neuronal nutrient associated with increased cognition and improved neurologic performance in human studies. Further features of our invention will be seen from the following examples which are given as exemplary:

Example 1

A biologic enhancing beverage was prepared by blending together the following ingredients: 12-16 oz. purified water, Citicoline (100 mg), Nicotinamide Riboside (NR) (100 mg), Coenzyme Q10 (50 mg), Hydroxyproline (100 mg), natural lemon-lime flavor crystals (6 mg), monk fruit natural sweetener crystals (200 mg), Sea Salt (5 mg) and Vitamin Complex [A (1 IU), B (1 mg), B2 (1 mg), B3 (3 mg), B6 (1 mg), B12 (100 mg), C (100 mg), D (50 IU), E (2 IU) and Folate (50 mcg)].

Example 2

A biologic enhancing beverage was prepared by blending together the following ingredients: 12-16 oz. purified water, Citicoline (200 mg), Nicotinamide Riboside (NR) (200 mg), Coenzyme Q10 (100 mg), Hydroxyproline (100 mg), natural coconut-lime flavor crystals (6 mg), monk fruit natural sweetener crystals (200 mg), Vitamin Complex (see example 1), and Sea Salt (5 mg).

Example 3

A biologic enhancing beverage was prepared by blending together the following ingredients: 12-16 oz. purified water, Citicoline (250 mg), Nicotinamide Mononucleotide (NMN) (250 mg), Coenzyme Q10 (150 mg), Hydroxyproline (150 mg), natural tropical punch flavor crystals (10 mg), Vitamin Complex (see Example 1), Guarana (100 mg), and Sea Salt (5 mg).

Example 4

A biologic enhancing beverage was prepared by blending together the following ingredients: 12-16 oz. of carbonated spring water, Citicoline (250 mg), Nicotinamide Mononucleotide (NMN) (250 mg), Coenzyme Q10 (150 mg), Hydroxyproline (150 mg), Vinpocetine (5 mg), natural orange flavor crystals (10 mg), Vitamin Complex (see Example 1), Guarana (200 mg), and Sea Salt (5 mg).

Example 5

A biologic enhancing beverage was prepared by blending together the following ingredients: 12-16 oz. of carbonated spring water, Citicoline (250 mg), Nicotinamide Riboside (NR) (250 mg), Coenzyme Q10 (200 mg), Hydroxyproline (150 mg), Vitamins Complex (see example 1), natural grapefruit flavor crystals (10 mg) and Sea Salt (5 mg).

Example 6

A biologic enhancing beverage was prepared by blending together the following ingredients: 12-16 oz. purified water, Citicoline (100 mg), Nicotinamide Riboside (NR) (100 mg), Coenzyme Q10 (50 mg), Hydroxyproline (100 mg), natural lemon-lime flavor crystals (6 mg), Allulose natural sweetener crystals (4 gr), Sea Salt (5 mg) and Vitamin Complex [A (1 IU), B1 (1 mg), B2 (1 mg), B3 (3 mg), B6 (1 mg), B12 (100 mg), C (100 mg), D (50 IU), E (2 IU) and Folate (50 mcg)].

The formulation of the present invention provides the foundation for a unique and novel hydration drink with improved capacity to enhance one's cognition and neurologic response, and recovery to physiologic and neurophysiologic, cardiophysiologic, and integument stressors and/or cell damage during athletics, training and following neuronal injury, cardiovascular stress, and integument injury.

Various changes may be made in our invention without departing from the spirit and scope thereof. For example, the formulation of the present invention may be formulated as a concentrate and diluted before use, or as an ingestible product in powder or solid form, or as a tablet or lozenge. Also, if desired, various flavor enhancing ingredients may be added to the formulation, including carbonation, a sweetener, a flavorant, an acidulant, a colorant, a vitamin, a mineral, an antioxidant, a preservative, an emulsifier, a thickening agent, a clouding agent, and combinations thereof. In some embodiment, the flavorant may comprise a natural fruit flavor preferably selected from the group consisting of orange, mandarin orange, blood orange, tangerine, clementine, grapefruit, lemon, lime, tangelo, apple, grape, pear, peach, nectarine, apricot, plum, prune, pomegranate, blackberry, blueberry, raspberry, strawberry, cherry, cranberry, currant, gooseberry, boysenberry, huckleberry, mulberry, date, pineapple, banana, mango, *papaya*, lychee, passion fruit, coconut, guava, kiwi, watermelon, cantaloupe, honeydew melon, and other natural fruits or derivative combinations thereof. In another embodiment the acidulant may be selected from the group consisting of citric acid, ascorbic acid, malic acid, lactic acid, tartaric acid, cinnamic acid, fumaric acid, maleic acid, adipic acid, glutaric acid, succinic acid, and/or other natural acidulants or derivative combinations thereof. Still other changes may be made without departing from the spirit and scope.

REFERENCES

1. Cohen, Deborah, "The truth about sports drinks". *BMJ* 2012; 345:e4737
2. Maughan R J et al. "Sports Drinks: Basic Science and Practical Aspects." CRC Press, Taylor & Francis, Inc., Philadelphia 2000; 1:1-304
3. Harris J L et al. "Sugary drink marketing to youth: Some progress but much room to improve" 2014. Rudd Center for Food Policy and Obesity. 2014 November
4. Faust M et al. "Oral Rehabilitation Salts (ORS)" World Health Organization (WHO) (UNICEF). Production of the New ORS 1985. WHO Document Production Services, Geneva, Switzerland: 1-59.
5. Harris J L et al. "Sugary Drinks FACTS in Brief" 2014. Rudd Center for Food Policy and Obesity. 2014 November www.sugarvdrinkfacts.org
6. Jacobs R A et al. "Improvements in Exercise Performance with High-Intensity Interval Training Coincide with an Increase in Skeletal Muscle Mitochondria Content and Function". *J Appl Physiol* 2013; 115(6):785-793.
7. Vanderthommen et al. "Electrical Stimulation as a Modality to Improve Performance of the Neuromuscular System". *Exercise and Sport Science Review,* 2007; 35(4): 180-185.
8. Gollnick et al. "Significance of Skeletal Muscle Oxidative Enzyme Enhancement with Endurance Training". *Clinical Physiology* 1982; 2(1):1-12.
9. Betts et al. "Systemic Indicies of Skeletal Muscle Damage and Recovery of Muscle Function After Exercise: Effect of Combined Carbohydrate-Protein Ingestion". *Appl. Physiol. Nutr. Metab.* 2009; 34: 773-784.
10. Banerjee et al. "Prolonged Electrical Muscle Stimulation Exercise Improves Strength and Aerobic Capacity in Healthy Sedentary Adults". *J Appl. Physiol.* 2005; 99(6): 2307-2311.

11. Seifert et al., "Health Effects of Energy Drinks on Children, Adolescents, and Young Adults", *PEDIATRICS* Vol. 127, Number 3, March 2011, pg. 511-528.
12. Popkin et al. "A New Proposed Guidance System for Beverage Consumption in the United States". *American Journal of Clinical Nutrition*, 2006; 83: 529-542.
13. The Nutrition Source, Harvard T. H. Chan School of Public Health, "Healthy Beverage Guidelines", 2017. www.hsph.havard.edu/nutrition/source/healthy-drinks-full-story.
14. "Summary." Institute of Medicine. 2005. *Dietary Reference Intakesfor Water, Potassium, Sodium, Chloride,* and Sulfate. Washington, D C: The National Academies Press. doi: 10.17226/10925.
15. Grieb P., "Neuroprotective Properties of Citicoline: Facts, Doubts and Unresolved Issues" *CNS Drugs* 2014; 28(3):185-193.
16. Secades, J. "Pharmacological and Clinical Review" 2010 Update. *Review of Neurology* 2011; 2, Suppl 2: S1-S48.
17. Givertz et al., "Role of Oxidative Stress in Heart Failure", Review of literature September 2018 www.uptodate.com.
18. Mortensen et al. "The Effect of Coenzyme Q10 on Morbidity and Mortality in Chronic Heart Failure: Results From Q-SYMBIO: A randomized Double-Blind Trial". *JACC Heart Failure* 2014; 2: 641-649.
19. Percival, M., "Nutritional Support for Connective Tissue Repair and Healing" *Clinical Nutrition Insights*, 1997 Rev. 6-98.
20. Adibhatla et al., "Citicoline: Neuroprotective Mechanisms in Cerebral Ischemia" *Journal of Neurochemistry* 2002; 80:12-23.
21. Skripuletz et al. "The Choline Pathway as a Strategy to Promote Central Nervous System (CNS) Remyelination", *Neural Regeneration Research* 2015 September; 10(9): 1369-1370.
22. Alvarez-Sabin J et al. "Long-term Treatment with Citicoline Prevents Cognitive Decline and Predicts a Better Quality of Life After a First Ischemic Stroke" *International Journal of Molecular Sciences* 2016; 17: 1-12.
23. Fioravanti et al. "Citicoline (Cognizin®) in the Treatment of Cognitive Impairment" *Clinical Interventions in Aging* 2006; 1 (3): 247-251.
24. McGlade E et al. "Improved Attentional Performance Following Citicoline Administration in Healthy Adult Women", *Food and Nutrition Science* 2012; 3(6): 769-773.
25. Skripuletz et al. "Pivotal Role of Choline Metabolites in Remyelination", *Brain, Journal of Neurology* 2015; 138: 398-413.
26. Tan H B et al. "Citicoline (CDP-Choline) for Traumatic Brain Injury (Protocol)", Cochrane Database of Systemic Reviews 2014; Issue 8 Article No.CDO-11217) OI:10.1002/14651858.CDO11217.
27. Zafonte et al. "The Citicoline Brain Injury Treatment (COBRIT) Trial: Design and Methods". *Journal of Neurotrauma* 2009; 26(12): 2207-2216.
28. Bruce et al. "Improvements in Concentration, Working Memory, and Sustained Attention Following Consumption of a Natural Citicoline-Caffeine Beverage", *Int J Food Sci Nutr December;* 65(8):1003-1007.
29. Grieb P., "Citicoline: A Food That May Improve Your Memory", *Medical Science Review* 2015; 2: 67-72.
30. Siliveri et al. "Citicoline Enhances Frontal Lobe Bioenergetics as Measured by Phosphorus Magnetic Resonance Spectroscopy" *NMR Biomed* 2008; 21(10):1066-1075.
31. Conant et al. "Therapeutic Applications of Citicoline for Stroke and Cognitive Dysfunction in the Elderly: A Review of the Literature", *Alternative Medicine Review* 2004; 9(1):17-31.
32. McGlade et al. "The Effect of Citicoline Supplementation on Motor Speed and Attention in Adolescent Males". *Journal of Attention Disorders*, 2015; pgs 1-14
33. Bruce, Steven, "Improvements in Quantitative EEG Following Consumption of a Natural Citicoline-Enhanced Beverage", *International Journal of Food Sciences and Nutrition*, June 2012; 63(4): 421-425.
34. Lozano R. "CDP-Choline in the Treatment of Cranio-Encephalic Traumata" *Journal of Neuroslogical Sciences* 1991; 103, Suppl:S43-S47.
35. McKee et al. "Chronic Traumatic Encephalopathy in Athletes: Progressive Tauopathy After Repetitive Head Injury", *J Neuropathol Exp Neurol* 2009; 68(7): 709-735.
36. Langlois et al. "The Epidemiology and Impact of Traumatic Brain Injury: A Brief Overview". *J Head Trauma Rehabil* 2006; Vol. 21, No. 5, 375-378.
37. Jafari, Mehdi, "Coenzyme Q10 in the treatment of heart failure: A systematic review of systematic reviews", *Indian Heart Journal* 70S (2018) S111-S117.
38. Prockop et al. "Relationship of Hydroxyproline Excretion in Urine to Collagen Metabolism: Biochemistry and Clinical Application", *Annals of Internal Medicine,* 1967; Vol. 66, No. 1243-1266.
39. Hausmann, Ernest et al., "Conversion of Proline to Hydroxyproline and Its Incorporation into Collagen", *The Journal of Biological Chemistry*, Vol. 236, No. 1, January 1961.
40. Citicoline. Open Search PubChem. National Library of Medicine National Center for Biotechnology Information, National Institute of Health, updated Nov. 11, 2017.
41. Citicoline. Monograph, Thorne Research Group. Alt Med Rev 2008; 13(1):50-57.
42. Zeisel, Steven H., "Choline: An Essential Nutrient for Public Health" *Nutr. Rev.* 2009 November 61(11): 615-623
43. Bradley R et al. "Coenzyme Q10 (CoQ10)" National Center for Complementary and Integrative Health, National Institute of Health, 2015 March: D489. www.nccih.nih.gov/D489.
44. "Coenzyme Q10 Introduction Monograph" Alt. Med. Rev. Volume 12, Number 2, June 2007:159-175.
45. "Hydroxyproline" PubChem Monograph. National Center for Biotechnology Information. National Library of Medicine, National Institute of Health, updated Nov. 11, 2017. www.pubchem. ncbi.nlm.nih.gov.
46. "Dietary Guidelines for Americans 2015-2020" Eighth Edition, USDA DietaryGuidlines.gov USDA Publication #: Home and Garden Bulletin No. 232
47. Vrentas, J. "MEDICAL CARE: Brett Farve and other NFL stars are backing the efforts of pharmaceutical companies to develop drugs that would treat football's concussion scourge" Sports Illustrated 2017 November; 18-19.
48. Ashley Welch CBS News "Sugary drinks lead to thousands of deaths, study finds", *CBS Interactive Inc.*, Jun. 30, 2015.
49. Clark, Wayne M. "Efficacy of citicoline as an acute stroke treatment" *Expert Opinion* Pharmacother. 2009, 10(5), pp 839-846.
50. Swithers S E, "Dangerous Effects of Artificial Sweeteners on Your Health" www.medicaldaily.com/4-dangerous-effects-of-artificial-sweeteners-on-your-health.

51. Alvarez-Sabin, Jose, M D. et al. "Citicoline in Vascular Cognitivie Impairment and Vascular Dementia After Stroke", *Stroke,* 2011, 42, suppl 1, S40-S43.
52. Secades, Julio J. et al., "Citicoline for Acute Ischemic Stroke: A Systematic Review and Formal Meta-analysis of Randomized, Double-Blind, and Placebo-Controlled Trials" *J of Stroke and Cerebrovascular Diseases* May 2016.
53. Adibhatla, R. M et la., "Mini-Review: Citicoline Mechanisms and Clinial Efficacy in Cerebral Ischemia" *Journal of Neuroscience Research,* 70: 113-139 (2002).
54. Zhou, Minghai et al., "Neronal death induced by misfolded prion protein is due to $NAD^+$ depletion and can be relieved in vitro and in vivo by $NAD^+$ replenishment", BRAIN, *J of Neurology* 2015: 138; 992-1008.
55. Yoshino, Jun et al., "$NAD^+$ Intermediates: The Biology and Therapeutic Potential of NMN and NR" *Cell Metabolism* Vol. 26, Mar. 7, 2018.
56. Suzuki, Eri et la., "Protective effect of nicotinamide against poly(ADP-ribose) polymerase-1-mediated astrocyte death depends on its transporter-mediated uptake" *Life Sciences* 86 (2010) 676-682.
57. Ying, Weihai, "Therapeutic potential of $NAD^+$ for neurological diseases", *Future Neurol.* (2007) 2(2), 129-132.
58. Ying, Weihai, "$NAD^+$/NADH and $NADP^+$/NADPH in Cellular Functions and Cell Death: Regulation and Biological Consequences" *Antioxidants & Redox Signaling* Vol. 10, No. 2, 2008.
59. Saini, Janmeet et al., "Nicotinamide Ameliorates Disease Phenotypes in a Human iPSC Model of Age-Related Macular Degeneration" *Cell Stem Cell* 20, 1-13, May 2017.
60. Pascual-Leon, Alvaro et al., "Chronic Traumatic Encephalopathy and Age of First Exposure to American-style Football" *Accepted Article*
61. Gong, Bing et al. "Nicotinamide riboside restores cognition through an upregulation of proliferator-activated receptor-γ coactivator 1α regulated β-secretase 1 degradation and mitochondrial gene expression in Alzheimer's mouse model" NIH Public Access Author Manuscript, *Neurobiol Aging* 2013 June; 34(6): 1581-1588.
62. Trammel, Samuel A. J., "Novel $NAD^+$ metabolomic technologies and their applications to Nicotinamide Riboside interventions". PhD thesis, University of Iowa, 2016.
63. Goody, Micelle et al., "A need for NAD+ in muscle development, homeostasis, and aging" Skeletal Muscle 2018, 8:9.
64. Gomes, Ana P. et al. "Declining $NAD^+$ Induces a Pseudohypoxic State Disrupting Nuclear-Mitochondrial Communication during Aging" *Cell* 155, 1624-1638, Dec. 19, 2013.
65. Magni, G. et al. "Enzymology and $NAD^+$ homeostasis in man" *CMLS Cellular and Molecular Life Sciences* 61 (2004) 19-34.
66. Yang et al., "Nutrient-Sensitive Mitochondrial $NAD^+$ Levels Dictate Cell Survival" *Cell* 130, 1095-1107, Sep. 21, 2007.
67. Das, Abhirup et al, "Impairment of an Endothelial $NAD^+$-$H_2S$ Signaling Network Is a Reversible Cause of Vascular Aging" *Cell* 173, 74-89 Mar. 22, 2018.
68. Fricker et al., "The Influence of Nicotinamide on Health and Disease in the Central Nervous System" *International Journal of Tryptophan Research* Vol. 11: 1-11, 2018.
69. Sauve, Anthony A. "NAD+ and Vitamin B3: From Metabolism to Therapies" *The Journal of Pharmacology and Experimental Therapeutics* March 2008, 324 (3) 883-893.
70. Canto et la., "The NAD+ Precursor Nicotinamide Riboside Enhances Oxidative Metabolism and Protects against High-Fat Diet-Induced Obesity" *Cell Metabolism* 15, 838-847, Jun. 6, 2012.
71. Belenky et al., "NAD+ metabolism in health and disease" *TRENDS in Biochemical Science* Vol. 32, No. 1, 2006.
72. Houtkooper et al., "The Secrect Life of NAD+: An Old Metabolite Controlling New Metabolite Signaling Pathways" *Endocrine Reviews*, April 2010, 31(2): 194-223.
73. Yoshino et al., "Nicotinamide Mononucleotide, a Key NAD+ Intermediate, Treats the Pathophysiology of Diet- and Age-Induced Diabetes in Mice" *Cell Metabolism* 14, 528-536, Oct. 5, 2011.
74. Gareri et al., "The role of citicoline in cognitive impairment: pharmacological characteristics, possible advantages, and doubts for an old drug with new perspectives" *Clinical Interventions in Aging,* 2015; 10: 1421-1429.
75. Lee et al. "Prion-like Mechanism in Amoyotrophic Lateral Sclerosis: are Protein Aggregates the Key?" *Ezperimental Neurobiology,* 2015 March: 24(1): 1-7.
76. Nonaka et al., "Prion-like Properties of Pathological TDP-43 Aggregates from Diseased Brains" *Cell Reports,* 4, Jul. 11, 2013, 124-134.
77. Nicolson, Garth L, "Mitochondrial Dysfunction and Chronic Disease: Treatment With Natural Supplements", *Alternative Therapies*, Vol. 20, Suppl. 1, 2014, pp 18-25.
78. Heneghan C et al. Forty Years of Sports Performance Research and Little Insight Gained. BMJ 2012; 345: e4797
79. Food and Drug Administration (FDS) Report. Energy Drinks and Supplements: Investigations of Adverse Event Reports. U S Food and Drug Administration, www.FDA-.gov
80. Sarter B. Coenzyme Q10 and Cardiovascular Disease: A Review. J Cardiovas Nursing 2002; 16(4):9-20.
81. Cundy T et al. Metabolic Bone Disease. Clinical Biochemistry: Metabolic and Clinical Aspects ($3^{rd}$ ed)2014, Elsevier Academic Press, Amsterdam; chapter 31:609-612.
82. Lozano F R. Efficacy and Safety of Oral CDP-Choline. Drug Surveillance Study in 2817 Cases. Arzneimittelforschung 1983; 33:1073-1080.
83. Kumanyika S et al. National Academies of Science, Engineering and Medicine Consensus Study Report, 2017: Principles of Developing Dietary Reference Intakes (DRI) Based on Chronic Disease. National Academies Press, 2017 Washington D. C. www:doi.org/10.17226/24828
84. Coenzyme Q10. PubChem Monograph. National Center for Biotechnology Information, National Library of Medicine, National Institute of Health, updated Nov. 11, 2017. www.pubchem.ncbi.nlm.nih.gov.

The invention claimed is:
1. A method for reducing symptoms of a disease in an individual in need thereof which method comprises administering to the individual a therapeutically effective amount of a ingestible formulation comprising Citicoline, CoQ10, hydroxyproline, and a niacinamide adenine dinucleotide (NAD+) precursor wherein the disease is a neurological disease.
2. The method of claim 1, wherein the neurological disease is a neurodegenerative disorder, and the formulation is administered twice daily.
3. The method of claim 1, wherein the formulation is administered as a liquid or suspension in a liquid carrier.

4. The method of claim 2, wherein the liquid carrier comprises water.

5. The method of claim 1, wherein the disease is an infectious neurological disease cause by spirochetes.

6. The method of claim 1, wherein the neurological disease is Lyme Disease or Syphilis.

\* \* \* \* \*